(12) United States Patent
Gurbel

(10) Patent No.: US 10,942,192 B2
(45) Date of Patent: *Mar. 9, 2021

(54) DETECTION OF RESTENSOSIS RISK IN PATIENTS RECEIVING A STENT

(71) Applicant: Paul A. Gurbel, Baltimore, MD (US)

(72) Inventor: Paul A. Gurbel, Baltimore, MD (US)

(*) Notice: Subject to any disclaimer, the term of this patent is extended or adjusted under 35 U.S.C. 154(b) by 252 days.

This patent is subject to a terminal disclaimer.

(21) Appl. No.: 16/199,552

(22) Filed: Nov. 26, 2018

(65) Prior Publication Data

US 2019/0137525 A1 May 9, 2019

Related U.S. Application Data

(63) Continuation of application No. 15/345,159, filed on Nov. 7, 2016, now Pat. No. 10,139,421, which is a continuation of application No. 14/943,939, filed on Nov. 17, 2015, now abandoned, which is a continuation of application No. 13/309,121, filed on Dec. 1, 2011, now Pat. No. 9,188,597, which is a continuation of application No. 11/663,599, filed as application No. PCT/US2006/038303 on Oct. 4, 2006, now Pat. No. 8,070,678.

(60) Provisional application No. 60/723,543, filed on Oct. 5, 2005.

(51) Int. Cl.
*G01N 33/86* (2006.01)
*G01N 33/49* (2006.01)

(52) U.S. Cl.
CPC ......... *G01N 33/86* (2013.01); *G01N 33/4905* (2013.01); *G01N 2800/323* (2013.01); *G01N 2800/52* (2013.01)

(58) Field of Classification Search
CPC ............... G01N 33/86; G01N 33/4905; G01N 2800/52; G01N 2800/323
USPC ....................................................... 600/369
See application file for complete search history.

(56) References Cited

U.S. PATENT DOCUMENTS

| 5,662,107 A | 9/1997 | Sakariassen |
|---|---|---|
| 7,563,454 B1 | 7/2009 | Pacetti |
| 2004/0186560 A1 | 9/2004 | Alt |
| 2005/0180886 A1 | 8/2005 | Bote Bote |

(Continued)

OTHER PUBLICATIONS

Chandrasekar B, and Tanguay JF. Platelets and restenosis. J Am Coll Cardiol. 2000 35(3):555-62.

(Continued)

*Primary Examiner* — Jacqueline Cheng
*Assistant Examiner* — Tho Q Tran
(74) *Attorney, Agent, or Firm* — Meunier Carlin & Curfman LLC

(57) ABSTRACT

Provided is a method of selecting a stent for implantation in the circulatory system of a human being. The method comprises obtaining a blood sample from a patient who requires implantation of a stent and testing said blood sample to determine a platelet coagulability level. The determined platelet coagulability level of said blood sample is compared with a threshold level of blood platelet coagulability. A determined platelet coagulability level above said threshold level indicates that a risk of restenosis is relatively high. If the determined platelet coagulability level is below said threshold level, a bare metal stent is selected. If the determined platelet coagulability level is at or above said threshold level, a drug-eluting stent is selected.

18 Claims, 3 Drawing Sheets

(56) References Cited

U.S. PATENT DOCUMENTS

2009/0142756 A1* 6/2009 Lundergan ........... C12Q 1/6883
                                                    435/6.17
2011/0045481 A1* 2/2011 Gladding ................ A61P 43/00
                                                    435/6.13
2016/0267243 A1* 9/2016 Zhao ...................... G16H 50/30

OTHER PUBLICATIONS

Gurbel PA, et al. platelet reactivity in patients and recurrent events post-stenting: results of the Prepare Post-Stenting Study. J Am Coll Cardiol. 2005 46(10):1820-6.
Lowe HC, et al. Coronary in-stent restenosis: current status and future strategies. J Am Coll Cardiol. 2002 39 (2):183-93.
Moreno R, et al. Drug-eluting stent thrombosis: results from a pooled analysis including 10 randomized studies. J Am Coll Cardiol. 2005 M45(6):954-9.
International Search Report for International Application No. PCT/US2006/038303, dated Jun. 17, 2008.
International Preliminary Report on Patentability for International Application No. PCT/US2006/038303, dated Mar. 24, 2009.
Written Opinion of the International Searching Authority for International Application No. PCT/US2006/038303, dated Jul. 8, 2008.

* cited by examiner

DETECTION OF RESTENSOSIS RISK IN PATIENTS RECEIVING A STENT

CROSS REFERENCE TO RELATED APPLICATIONS

This application is a continuation of U.S. patent application Ser. No. 15/345,159, filed on Nov. 7, 2016, which is a continuation of Ser. No. 14/943,939, filed on Nov. 17, 2015, which is a continuation of Ser. No. 13/309,121 filed on Dec. 1, 2011, now U.S. Pat. No. 9,188,597, which is a continuation of Ser. No. 11/663,599, filed on Mar. 23, 2007, now U.S. Pat. No. 8,070,678, which is the National Stage of International Application No. PCT/US06/38303, filed on Oct. 4, 2006, which claims the benefit of U.S. Provisional Application No. 60/723,453, filed on Oct. 5, 2005. The applications to which the present application claims benefit are herein incorporated by reference in their entireties.

FIELD OF THE INVENTION

The present invention relates to assessing the risk of developing restenosis in patients treated with stents with atherosclerotic vascular disease and using the risk assessment to determine the intensity of antiproliferative therapy administered to the vascular wall by means of a drug-eluting stent.

BACKGROUND OF THE INVENTION

Restenosis remains a major limiting factor in the percutaneous treatment of coronary artery disease. Despite improvements in restenosis rates achieved from the use of stents and the introduction of drug-eluting stents, restenosis persists in a small percentage of patients. The sequence of events contributing to restenosis is initiated at the stent site as a result of arterial wall trauma, endothelial injury and the release of growth factors, chemoattractants, and inflammatory mediators. These events induce platelet and leukocyte activation and trigger the coagulation cascade. Although the underlying pathophysiology is not uniformly accepted, major pathological findings in acute or chronic stent failure include the deposition of fibrin and platelets, suggesting that a key event in development of restenosis is thrombus formation.

Treatment with stents reduces restenosis compared to balloon angioplasty and now drug-eluting stents have further reduced restenosis rates. However, it is well recognized that most patients treated with bare metal stents develop clinically irrelevant degrees of intimal proliferation and therefore would not necessarily have benefited from the implantation of a drug-eluting stent. See R. Moreno, et al., Drug-eluting stent thrombosis: results from a pooled analysis including 10 randomized studies; J Am Coll Cardiol. 2005; 45: 9549. Nevertheless, the current practice is to implant the more costly drug-eluting stents in the majority of patients undergoing percutaneous intervention. See H. C. Lowe, et al., Coronary in-stent restenosis: current status and future strategies; J Am Coll Cardiol. 2002; 39: 183-93. The ability to predict which patients are most prone to developing neointimal formation could lead to more selective use of drug-eluting stents and tailor the intensity of antiproliferative therapy.

Platelet-related periprocedural thrombotic and inflammatory processes that influence neointimal hyperplasia and angiogenesis are considered important risk factors for restenosis. See B. Chandrasekar et al., Platelets and restenosis; J Am Coll Cardiol. 2000; 35: 555-62. In addition, preexisting inflammatory mediators and hypercoagulable factors have also been proposed to influence the process. Despite an established mechanism linking thrombogenesis to the restenosis process, there are few data in humans that have examined the relation of ex vivo measurements of platelet reactivity to restenosis. This information might be clinically useful in evaluating patients undergoing Percutaneous Cardiovascular Intervention (PCI) to identify a subgroup who may benefit from more aggressive therapy aimed at disrupting the sequence of events leading to restenosis. The ability to predict which patients are most prone to developing neointimal formation could also lead to more selective use of the more costly drug-eluting stents (DES). Use of DES has reduced restenosis rates. Currently, DES are routinely implanted in the majority of patients undergoing PCI without consideration as to whether the clinically irrelevant degrees of intimal proliferation that develop in most patients treated with bare metal stents warrant this practice. Moreover, there is concern that DES have a greater risk of thrombosis than bare metal stents.

At this time, there is no uniformly accepted method to determine which patients are at greatest risk for developing stent restenosis. A major cost savings would result from a method that reliably predicted those patients at greatest risk. These patients would be treated with the more costly drug-eluting strategy whereas those at minimal risk would receive the less expensive bare metal stent. It is well known that specific angiographic and clinical features are associated with a higher risk of restenosis. These include the presence of diabetes, small vessels, long lesions and bifurcation disease. In addition, a strategy that determines who will benefit from DES will entail much less use of dual antiplatelet therapy that is required indefinitely in patients treated with DES due to the excess hazard of stent thrombosis.

Presently, there are no laboratory tests that predict the occurrence of restenosis. Platelets play a fundamental role in the genesis of stent restenosis by modulating coagulation, inflammation, and smooth muscle proliferation. Thrombi with high tensile strength may facilitate neointimal hyperplasia at the stent site. Platelet-related periprocedural thrombotic and inflammatory processes that influence neointimal hyperplasia and angiogenesis are considered important risk factors for restenosis in animal models. See P. A. Gurbel, et al., Platelet reactivity in patients and recurrent events post-stenting: results of the PREPARE POST-STENTING Study; J Am Coll Cardiol. 2005; 46: 1820-26. Despite these established mechanisms, there are few data in humans that examined the relation of ex vivo measurements of platelet reactivity to restenosis. Moreover, preexisting inflammatory and hypercoaguable factors have also been proposed as important factors influencing restenosis. Moreover, patients with rapid thrombin generation would be expected to readily form thrombi.

There is a need in the field for a method to accurately risk-stratify patients for restenosis. This methodology would therefore tailor patient therapy during stent implantation. This method would assist in the decision making for using a bare metal stent versus a drug-eluting stent and, moreover, would also determine the intensity of drug delivery based on the individual patient's risk.

SUMMARY OF THE INVENTION

The invention features methods and compositions for assessing the risk of developing restenosis in patients with vascular disease undergoing stenting. The invention is based on the discovery that a platelet mediated hypercoaguable state is an important risk factor for the development of restenosis and identifies patients with the highest risk of needing a subsequent revascularization procedure. Accompanying the platelet-mediated hypercoaguable state is the presence of rapid fibrin-platelet clot formation which is a marker of the speed and intensity of thrombin generation; and a strong platelet-fibrin clot (i.e. high tensile strength). Therefore, any tool that can measure platelet-mediated hypercoaguability would be expected to predict restenosis. In my experiments, I measured these properties (i.e., the speed of thrombin generation by the parameter, R, and the strength of the platelet-fibrin clot by the parameter, MA) by thrombelastography, but other methods including enzyme linked immunosorbent assays to measure thrombin generation and devices to measure platelet reactivity including aggregometers, and flow cytometry and other tools that measure the viscoelastic properties of the clot would be expected to predict restenosis.

In an embodiment of particular interest, the risk of developing restenosis is assessed by determining the maximum tensile strength of the clot formed in the blood of the particular patient after stimulating the blood with an agonist that generates thrombin. The restenosis score is then measured and the individual risk is assessed based on the relation of the score to a chosen threshold level. The risk level is then used as a guide to determine whether to treat the patient with a bare metal stent as compared to a drug-eluting stent. In those patients with the highest risk, the most intensive drug delivery is chosen.

The invention is advantageous in that, prior to the invention, no readily available or accepted methodology was available to assess the risk for restenosis of the individual patient undergoing coronary stenting. Current practice is to treat patients with drug-eluting stents irrespective of an assessment of their risk for restenosis. Drug-eluting stents are expensive and require prolonged therapy with expensive antiplatelet agents. Many patients are intolerant of prolonged antiplatelet therapy and therefore, if the antiplatelet therapy is stopped, they are at risk for thrombosis. Patients treated with drug-eluting stents are also at greater risk for late stent thrombosis than patients treated with bare metal stents. These factors are important limitations to the uniform use of drug-eluting stents. Thus, the invention provides a method to risk stratify patients undergoing stenting in order to appropriately choose whether a drug-eluting stent is necessary. Based on the risk assessment, those patients above a specific threshold would receive a DES and may also receive a higher dose of the antiproliferative drug or an alternative antiproliferative drug(s) as compared to patients at a lower risk threshold.

The present invention is based on the discovery that the maximum tensile strength of a clot, and more specifically, the maximum clot strength as measured by thrombelastography is a powerful marker of the risk of restenosis in patients treated with stents for obstructive coronary artery disease. Importantly, maximum clot strength has been found to be an effective marker of the risk of restenosis irrespective of clinical and angiographic variables.

Prior to the invention, there was no readily available method to assess restenosis risk. More importantly, knowledge of the patient's risk for restenosis is invaluable in preventing complications as those patients in the highest risk group would be most carefully followed clinically.

Prior to the invention, the drug dose delivered by the drug-eluting stents was uniform; a choice of dose was unavailable. The invention provides a scheme for the implementation of various drug doses based on the patient's risk profile.

In one embodiment, the patient has his/her blood drawn prior to the stent procedure. The blood is analyzed by thrombelastography and the maximum tensile strength of the clot is recorded. The clot usually is stimulated to form by the addition of kaolin, but other agonists that activate the generation of thrombin can also be used. The tensile strength of the given clot is then assessed for restenosis risk based on the known distribution of tensile strength measured in patients with coronary artery disease. The patient can then be placed in a risk group based on the quartile of clot strength. For example, the $1^{st}$ quartile is associated with the lowest risk, the $2^{nd}$ quartile with a higher risk and so forth up to the $4^{th}$ quartile where risk is greatest. Based on the quartile of clot strength, the decision for the particular stent can be made. In those patients with $2^{nd}$-$4^{th}$ quartile clot strength, drug-eluting stents should be considered, whereas in those patients with the lowest quartile, a bare metal stent would be chosen.

Accordingly, it is a first object of the present invention to detect restenosis risk in patients receiving a stent by measuring maximum thrombin-induced clot strength.

It is a further object of the present invention to provide such a method in which the relative risks of respective patients are quantified based upon four quartiles of clot strength.

It is a yet further object of the present invention to provide such a method in which those patients falling within the lowest quartile(s) would be treated with bare metal stents.

It is a still further object of the present invention to provide such a method in which those patients falling within the highest quartile(s) would be treated with a stent coated with a drug-eluting substance.

It is a still further object of the present invention to provide such a method in which judgments would be made concerning those patients falling within the middle 2 quartiles as to whether they are suitable for a bare metal stent or a stent coated with a drug-eluting substance.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1A:
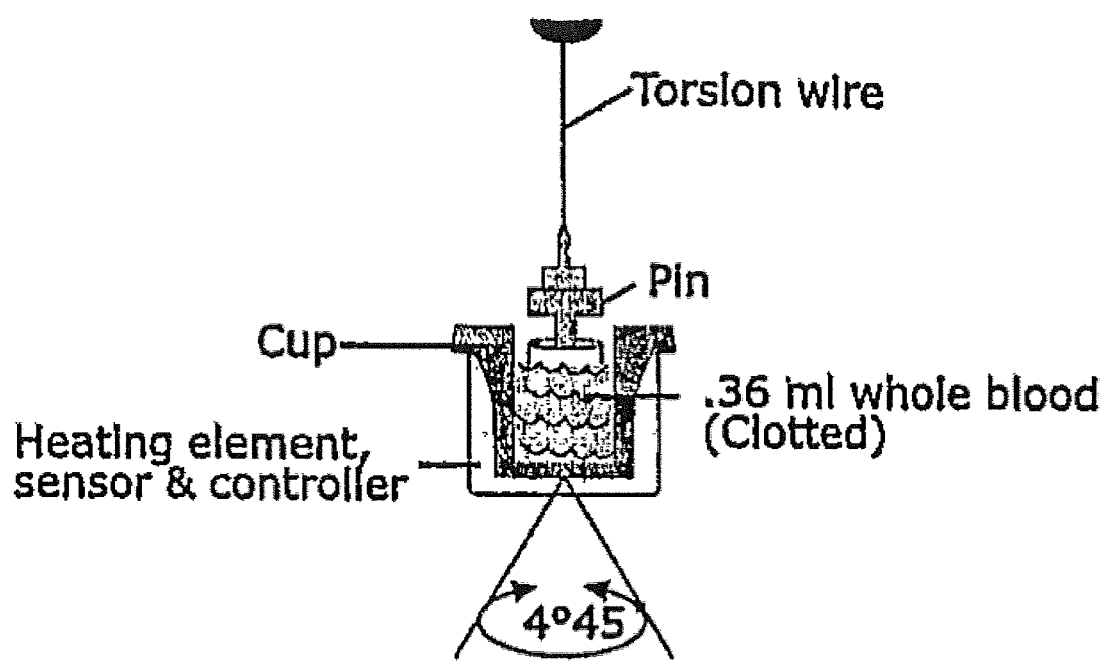
FIG. 1a shows a schematic representation of the structure of a TEG hemostasis analyzer.

Platelets play a fundamental role in the genesis of stent restenosis by mediating inflammation and smooth muscle proliferation. Thrombi with high tensile strength may facilitate growth factor release to the adjacent vessel wall resulting in neointimal hyperplasia.

Applicant measured pretreatment ex vivo maximum thrombin-induced clot strength, time to fibrin formation, and the combined clotting index with thrombelastography (TEG) in 178 consecutive patients undergoing elective stenting of de novo (n=160) and restenotic lesions (n=18) and in 25 healthy controls. Patients were followed for 6 months for the development of symptomatic restenosis. Patients who developed restenosis (n=28) had greater maximum clot strength (71.0±5.0 vs. 66.1±7.0, p=0.0004), higher combined clotting indices (3.4±1.8 vs 2.1±2.3, p=0.005) and more rapid fibrin generation times (4.0±1.0 vs 4.8±1.7, p=0.03) than patients without restenosis and healthy controls (p<0.05 for all measurements). The relative risk of developing restenosis was 22.5 times greater for patients with clot strength in the highest quartile vs. the lowest quartile. Multivariate analysis demonstrated the independent predictive value of these laboratory measurements.

These results suggest that the prothrombotic state, measured by TEG and highlighted by increased clot strength, is independently predictive of the development of in-stent restenosis. High clot strength may serve as a new marker leading to patient-specific therapies targeting antiproliferative therapy for those at greatest risk.

Presently, platelet related periprocedural thrombotic and inflammatory processes that influence neointimal hyperplasia and angiogenesis are considered as important risk factors for restenosis. Despite these established mechanisms, there are few data in humans that examine the relation of ex vivo measurements of platelet reactivity to restenosis. Moreover, preexisting inflammatory and hypercogulable factors are also suggested as important factors influencing restenosis. Applicant has found that patients with high clot strength may be at greatest risk for restenosis since their thrombi may be most resistant to disruption by flowing blood. A robust clot would theoretically facilitate residence of platelets at the vessel wall and subsequent delivery of pro-restenotic factors. Moreover, patients with rapid thrombin generation would be expected to readily form thrombi.

The Investigational Review Board at Sinai Hospital of Baltimore approved a study resulting in development of the present invention. One hundred and seventy-eight consecutive patients who underwent successful elective coronary artery or saphenous vein graft stenting gave informed consent prior to the procedure and were prospectively followed post-discharge for the development of symptomatic restenosis. Inclusion criteria included patients over 18 years old. Exclusion criteria were a history of bleeding diathesis, acute myocardial infarction within 48 hours, elevated cardiac markers (above upper limits normal for the respective assay), cerebrovascular event within 3 months, chronic vessel occlusion or angiographically visible thrombus, illicit drug or alcohol abuse, prothrombin time greater than 1.5 times control, platelet count<100,000/mm$^3$, hematocrit<30%, creatinine>4.0 mg/dl, and glycoprotein (GP) IIb/IIIa inhibitor use prior to the procedure.

Blood samples were obtained in the catheterization laboratory through an indwelling femoral vessel sheath and transferred to vacutainer collecting tubes (Becton-Dickinson, Rutherford, N.J.) containing 40 USP lithium heparin after discarding the first 2-3 ml of free flowing blood. Samples were obtained before GPIIb/IIIa inhibitors and heparin administration (baseline). Blood samples were also obtained at the time of the second procedure from patients who developed symptomatic restenosis.

Figure 1B:
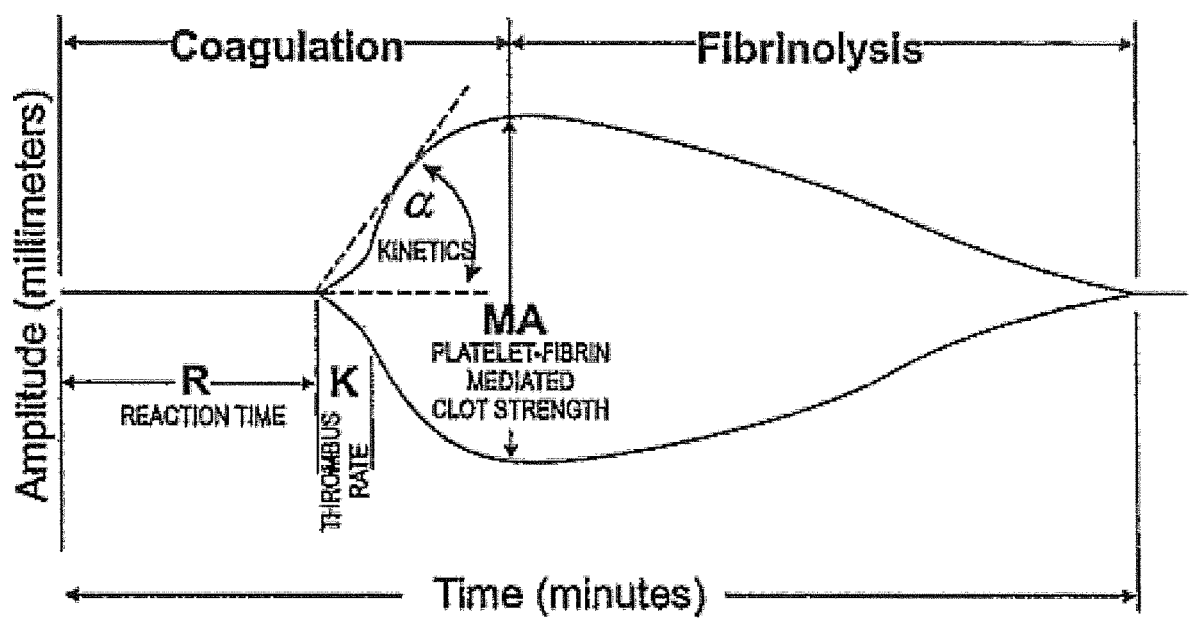
FIG. 1b shows a graph of amplitude of the thrombin-generated clot versus time.

The Thrombelastograph (TEG®) Hemostasis Analyzer with automated analytical software provides quantitative and qualitative measurements of the physical properties of a clot. Briefly, the TEG is a viscoelastic monitor that measures the degree of platelet-fibrin mediated clot strength as shown in FIG. 1a. Fibrin strands in the blood sample link a rotating sample cup with a stationary pin suspended by a torsion wire. The torque of the rotating cup is transmitted to the immersed pin. Pin movement is converted to an electrical signal by a transducer and is interpreted by the computer to create a tracing. The degree of platelet contribution to the clot strength through platelet-fibrin bonding directly influences the magnitude of pin movement and ultimately the amplitude of the tracing. In the present study, the maximum amplitude of the thrombin-generated clot [(MA) (mm)], the time from the start of the sample run to the first significant levels of clot formation [reaction time (R) (min)] and Coagulation index (CI) were measured. A representative signature waveform is shown in FIG. 1b. The resultant hemostasis profile can be evaluated with individual points in the profile indicating specific parameters of patient hemostasis.

The R parameter is a measure of initial thrombin-generated fibrin formation and has been correlated with the velocity of thrombin generation. The coagulation index (CI) is a measure of overall coagulation that is calculated from the kinetics of clot development and formation in native or kaolin-activated whole blood. CI is derived from a computer calculated linear combination of R, K [the rate of thrombus formation], MA and the α-angle [a measure of the rapidity of fibrin generation and cross linking according to the following formula]:

$$(CI=-0.6516R-0.3772K+0.1224MA+0.0759\alpha-7.7922).$$

Normal values for the CI lie between −3.0 and +3.0, which is equivalent to three standard deviations about the mean of zero. Positive values outside this range (CI>+3.0) indicate that the sample is hypercoagulable, whereas negative values outside this range (CI<−3.0) indicate that the sample is hypocoagulable.

Blood was analyzed according to the manufacturer's instructions. One mL of heparinized blood was transferred to a vial containing kaolin and mixed by inversion. Five hundred microliters of the activated blood was then transferred to a vial containing heparinase and mixed to neutralize the heparin. The neutralized blood (360 uL) was immediately added to a heparinase coated cup and assayed in the TEG analyzer according to the manufacturer's instructions to obtain the thrombin-induced clot. Once the sample assay is completed, automated analytical software generates the MA, R and CI values.

Patients were clinically followed by research staff for the development of recurrent angina defined as the occurrence of typical symptoms that warranted cardiac catheterization at the discretion of the treating cardiologist who was blinded to the study results of the given patient. Restenosis was defined as >50% luminal diameter stenosis in the stented segment by visual estimate. Stent thrombosis was defined by the sudden onset of coronary artery occlusion in a stented vessel resulting in hospitalization and judged by the treating interventionalist as due to thrombosis.

The linear logistic regression model was employed to fit the binary data (restenosis=1 and no-restenosis=0). This logistic regression model was fit using SAS procedure PROC LOGISTIC (Cary, N.C., USA). The model is given by:

$$\text{Logit}(p)=\text{Log}\{p/(1-p)\}=\beta_0+\beta_1 \cdot X$$

where p=proportion of incidence of restenosis, and X is a predictor variable. The three variables (possible X) considered here are MA, LTA and R. $\beta_0$ is constant or intercept (value of the dependent variable when X=0); $\beta_1$ is the slope (increase in the value of p per unit increase in X).

The multiple linear logistic regression model was employed to fit binary data to compare the prevalence of demographic, angiographic and clotting variables in patients with restenosis and without restenosis. The logistic regression model was fit using SAS procedure PROC LOGISTIC. Odds ratios were calculated using SAS software, and ROC curves were generated using MedCalc Software (MedCalc Software, Broekstraat, Belgium). Based on the normal distribution of data the mean±SD is reported except as otherwise noted and p<0.05 was considered significant. Comparisons were made between the restenotic and non-restenotic groups by t-tests (Statistica software) for continuous variables and by Fischer's exact test for categorical data.

The results were as follows:

One hundred thirty-three patients received a loading dose of clopidogrel [300 mg (n=76), 600 mg (n=57)] in the catheterization laboratory immediately after successful stenting. Patients on a maintenance dose of clopidogrel at the time of admission (n=45) did not receive a loading dose. The GP IIb/IIIa inhibitor, eptifibatide was administered to 71 patients at the discretion of the treating physician. All patients treated with eptifibatide received unfractionated heparin according to the Enhanced Suppression of the Platelet IIb/IIIa Receptor with Integrilin Therapy (ESPRIT) dosing regimen (60 U/kg) as a bolus. In all other patients, heparin was administered to achieve an activated clotting time of 300 seconds. Aspirin (325 mg) was administered on the day of the procedure and daily thereafter. The maintenance dose of clopidogrel was 75 mg daily.

One hundred and sixty patients underwent stenting of de novo lesions and 18 patients underwent stenting of at least one restenotic lesion. Symptomatic restenosis developed in 12 patients over the 6 months of follow-up (10/160 initially treated with de novo lesions land 2/18 initially treated with at least one restenotic lesion). 4 patients developed a myocardial infarction in the distribution of the target vessel. Among the latter patients, 2 events were due to obstruction of the stented segment, and 2 patients had the frank occurrence of a subacute stent thrombosis (Tables 5, 6).

Healthy controls comprised 50% men at an age of 39±8 years and were free of cardiovascular risk factors and concomitant pharmacologic therapy. The clinical and angiographic demographics of patients with and without symptom driven restenosis are shown in Tables 1 and 2 and demonstrate equivalence between the groups except for a higher incidence of prior myocardial infarction in patients who developed restenosis.

Maximum Clot Strength, Rapidity of Fibrin Formation, and Clot Index

Baseline Measurements

Patients undergoing stenting had markedly higher MA (67.0±6.0) and CI (2.3±2.0); and more rapid fibrin generation (4.7±1.5) than healthy controls (p<0.001 for all comparisons, Table 3). Patients undergoing treatment of restenotic lesions had higher baseline MA (69.9±3.0 vs. 67.0±6.0, p=0.04) and CI (3.6±1.5 vs. 2.2±2.2, p=0.005), and shorter R (3.7±1.2 vs. 4.8±1.6, p=0.009) than patients undergoing treatment of de novo lesions.

Figure 2:
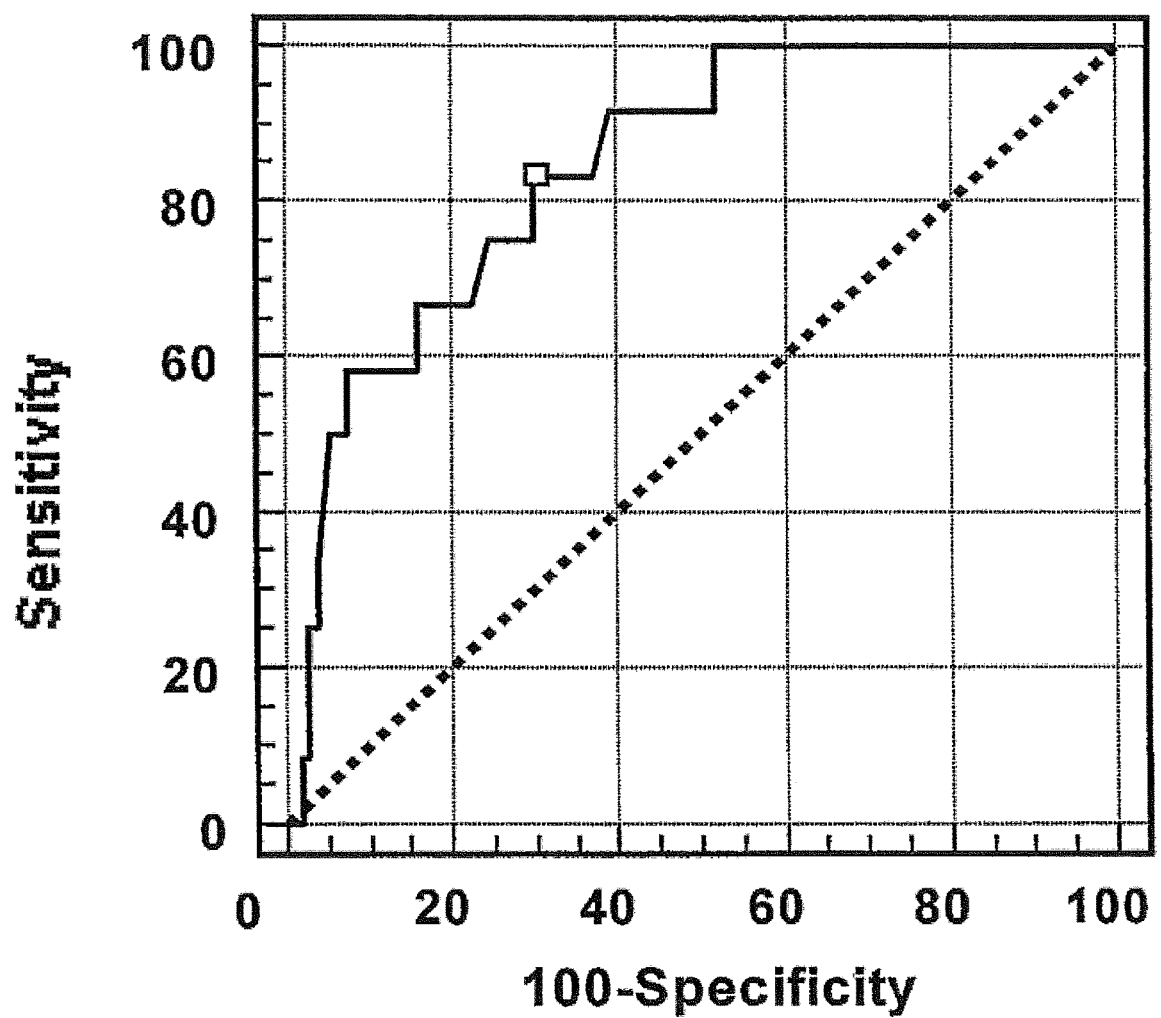
FIG. 2 shows a bar graph comparing patients without restenosis with patients with restenosis including values for maximum amplitude of platelet-fibrin mediated clot strength in millimeters (MA) of less than 72 and greater than 72, respectively.

The mean normal value+2SD (72 mm) for MA (MA72) was evaluated to determine whether patients might be classified by restenosis risk based on having pre-treatment values above or below this high level of platelet-fibrin mediated clot strength (Table 4). Of the 12 patients who suffered restenosis, 8 had MA values above 72 mm (67%), compared with 30 of 150 patients (20%) who did not develop restenosis (p=0.0005). The odds ratio (OR) of symptomatic restenosis at 6 months post-PCI for patients with MA values greater than 72 mm was 10.9. Use of MA72 to differentiate risk of restenosis among post-PCI patients had a sensitivity of 67% and a specificity of 80% (FIG. 2). Using the ROC curves, the sensitivity and specificity are similar to the Table 4 results, with a sensitivity of 67% and a specificity of 83%. Eleven out of 12 (92%) patients with restenosis had MA values in the $3^{rd}$ and $4^{th}$ quartiles (MA>68); eight out of 12 (67%) were in the $4^{th}$ quartile (MA>72).

Overall, patients who developed restenosis had higher baseline maximum clot strength (75.5.±4.5 vs. 66.5±6.5, p=0.0001), more rapid fibrin generation (4.2±1.0 vs. 4.6±1.5, p=0.36), and a greater clot index (3.6±1.3 vs. 2.3±2.31 p=0.03) than patients who did not develop restenosis. Comparison of measurements with respect to the initial treatment of de novo vs. restenotic lesions demonstrates that high clot strength, rapid fibrin generation and a great clot index were associated with restenotic lesions. Similar findings occurred in the baseline analyses from the immediate study that demonstrated higher clot strength, more rapid fibrin generation and a greater clot index in those patients undergoing revascularization for stent restenosis as compared to treatment of a de nove lesion (Table 3).

The relative risk ratios for restenosis for each of the quartiles as compared to the first quartile based on the baseline measurements from both groups are shown in Table 4.

Discussion

The current study demonstrates that: 1) The physical properties of ex vivo thrombi generated by thrombin in the blood of patients undergoing elective stenting differs dramatically from the thrombi generated in healthy controls. Patient thrombi have markedly greater maximum tensile strength and fibrin production occurs more rapidly, 2) The physical properties of ex vivo thrombi differs between patients undergoing treatment of de novo lesions versus patients undergoing treatment of restenotic lesions. Patients with restenotic lesions have greater thrombin-induced clot strength and produce fibrin more rapidly than patients undergoing treatment of de novo lesions, and 3) Baseline measurements of maximum thrombin-induced clot strength are highly predictive of restenosis; patients in the highest quartile have an approximate 23 fold risk of developing restenosis as compared to patients in the lowest quartile. Applicant's data demonstrates that these measurements are stable over the period of restenosis development.

The current study is the first to examine the predictive value of the physical properties (i.e. maximum tensile strength) of a patient's clot in determining restenosis. Moreover, it is the first study to assess the utility of thrombelastography measurements as markers for restenosis development in patients undergoing percutaneous coronary revascularization. Moreover, Applicant's data demonstrates the independent predictive value of the measurements irrespective of the clinical demographics that have been associated with restenosis.

The current study strengthens the proposed central role of reactive platelets in the pathophysiology of restenosis. The maximum thrombin-induced clot strength measured by TEG is indicative of the tensile properties of the platelet-fibrin interaction. Applicant had hypothesized that robust clot formation may facilitate platelet residence at the vessel wall interface and thus enhance the transfer of growth factors, thus promoting intimal proliferation and restenosis. Platelet and fibrin deposition has been well described at the site of stent implantation. Platelet surface receptors facilitate attachment of leukocytes to the area of injury that further release growth factors. Moreover, in the current study, patients with the most rapid thrombin generation may be expected in vivo to generate activated platelets. Applicant's data supports the importance of the rapidity of thrombin generation and the responsiveness of platelets to thrombin as major factors in the development of restenosis.

It is well known that many patients experience excellent long-term clinical outcomes following treatment with non-drug eluting stents. In addition, there are pitfalls to the implantation of drug-eluting stents that include a requirement of prolonged dual antiplatelet therapy and concerns for late stent thrombosis. Prolonged therapy with clopidogrel adds significantly to cost and many patients are intolerant to treatment. Up to this date, there have been no validated markers that predict restenosis. The validation of a restenosis marker may assist in the decision making for a bare metal stent as compared to a drug-eluting stent. Applicant's data strongly suggests that patients in the lowest quartile for clot strength are at very low risk of developing restenosis whereas those in the highest quartile have extremely high risk. These quartiles may serve as cutpoints to be examined in prospective investigations of bare metal versus drug-eluting stents.

Applicant's results suggest that the prothrombotic state measured by TEG and highlighted by increased clot strength is independently predictive of the development of in-stent restenosis. High clot strength may serve as a new marker leading to patient-specific therapies targeting antiproliferative therapy for those at greatest risk.

As such, an invention has been disclosed in terms of preferred embodiments thereof which fulfill each and every one of the objects of the invention as set forth hereinabove, and provide a new and useful method for the detection of restenosis risk in patients receiving a stent by measuring the characteristics of blood clotting including the measurement of maximum thrombin-induced clot strength of great novelty and utility.

Of course, various changes, alterations and modifications in the teachings of the present invention may be contemplated by those skilled in the art without departing from the intended spirit and scope thereof.

As such, it is intended that the present invention only be limited by the terms of the appended claims.

TABLE 1

Patient Demographics

| | Restenosis (n = 12) | No Restenosis (n = 166) | p-value |
|---|---|---|---|
| Age (years) | 66 ± 9 | 64 ± 12 | NS |
| Race (Caucasian) n, (%) | 6 (50) | 121 (73) | .03 |
| Gender (Male) n, (%) | 4 (33) | 109 (66) | .007 |
| BMI | 30 ± 6 | 30 ± 7 | NS |
| Risk Factors/Past medical Hx n, (%) | | | |
| Smoking | 9 (75) | 86 (52) | .05 |
| Family history of CAD | 6 (50) | 91 (55) | NS |
| Hypertension | 6 (50) | 105 (63) | NS |
| Hyperlipidemia | 10 (83) | 126 (76) | NS |
| Diabetes | 5 (42) | 73 (44) | NS |
| Prior Myocardial Infarction | 7 (58) | 48 (29) | .009 |
| CHF | 3 (25) | 24 (14) | NS |
| Prior CABG | 4 (33) | 42 (25) | NS |
| Prior PTCA | 5 (42) | 44 (27) | NS |

TABLE 1-continued

Patient Demographics

| | Restenosis (n = 12) | No Restenosis (n = 166) | p-value |
|---|---|---|---|
| Baseline Medications n, (%) | | | |
| Aspirin | 12 (100) | 166 (100) | NS |
| Clopidogrel | 2 (17) | 43 (26) | NS |
| Beta blockers | 8 (67) | 147 (89) | .01 |
| ACE Inhibitors | 9 (75) | 117 (70) | NS |
| Calcium blockers | 2 (17) | 39 (23) | NS |
| Lipid lowering agents | 11 (92) | 142 (86) | NS |
| 3A4 | 10 (82) | 91 (55) | NS |
| Non 3A4 | 1 (8) | 51 (31) | NS |
| Laboratory Data | | | |
| WBC (×1000/mm$^3$) | 7.8 ± 2.6 | 7.3 ± 2.2 | NS |
| Platelets (×1000/mm$^3$) | 263 ± 82 | 236 ± 69 | NS |
| Hematocrit (g/dl) | 37.7 ± 5.5 | 40.0 ± 5.0 | NS |
| Hemoglobin (g/dl) | 12.2 ± 2.3 | 13.4 ± 1.9 | NS |
| Creatinine (g/dl) | 1.0 ± 0.3 | 1.1 ± 0.5 | NS |

BMI = body mass index

CABG = coronary artery bypass graft surgery

CAD = coronary artery disease

PTCA = percutaneous coronary angioplasty

ACE = angiotensin converting enzyme

WBC = white blood cells

3A4 = hepatic cytochrome 3A4

TABLE 2

Procedural Characteristics

| | Restenosis (n = 12) | No Restenosis (n = 166) | p Value |
|---|---|---|---|
| Ejection Fraction (%) | 46 ± 12 | 50 ± 8 | NS |
| Number of vessels treated | 1.3 ± .5 | 1.3 ± .6 | NS |
| Lesion Morphology | | | |
| Denovo n, (%) | 10 (83) | 150 (90) | NS |
| Lesion Location n, (%) | | | |
| LAD | 4 (34) | 54 (33) | NS |
| CX | 1 (8) | 44 (27) | .07 |
| RCA | 7 (58) | 61 (36) | .06 |
| SVG | 0 | 7 (4) | NS |
| Stent Types | | | |
| Drug eluting n, (%) | 8 (66) | 116 (70) | NS |
| Reference vessel diameter (mm) | 3.1 ± 0.4 | 3.0 ± 0.4 | NS |
| Total lesion length (mm) | 24 ± 13 | 19 ± 12 | NS |
| Pre-stenosis (%) | 88 | 85 | NS |
| Post-stenosis (%) | 5 | 4 | NS |

CX = circumflex artery

LAD = left anterior descending artery

RCA = right coronary artery

SVG = saphenous vein graft

TABLE 3

Clot Strength, Reaction Time, Coagulation Index in Healthy Controls and Patients with Baseline Denovo and Restenotic Lesions

| | | Patients with Baseline De novo Lesions | | | Patients with Baseline Restenotic Lesions | | |
|---|---|---|---|---|---|---|---|
| | | No Restenosis | Restenosis (n = 10) | | No Restenosis | Restenosis (n = 2) | |
| | Healthy Controls (n = 25) | (n = 150) Baseline Measurement | Baseline Measurement | At time of PCI for restenosis | (n = 16) Baseline Measurement | Baseline Measurement | At time of PCI for recurrent restenosis |
| Clot Strength (MA) (mm) | 60.7 ± 5.1 | 66.2 ± 7.0* | 75.0 ± 4.7** | 77.4 ± 4.4 | 68.5 ± 3.1 | 76.5 ± 1.0$^\Psi$ | 76.6 ± 1.1 |
| Reaction Time (R) (min) | 6.9 ± 1.2 | 4.8 ± 1.7* | 4.8 ± 1.2 | 4.6 ± 1.5 | 4.0 ± 1.1 | 2.0 ± 0.5$^\#$ | 2.0 ± 0.5 |
| Coagulation Index (CI) | −0.8 ± 1.8 | 2.1 ± 2.3* | 3.1 ± 1.6 | 3.8 ± 1.4 | 3.2 ± 1.3 | 5.9 ± 0.4$^\delta$ | 6.0 ± 0.5 |

*p < 0.001 Healthy controls vs. patients with baseline de novo lesions who did not develop restenosis
**p < 0.001 Patients with baseline de novo lesions who did not develop restenosis vs. who developed restenosis
$^\Psi$p = 0.02 Patients with Baseline Restenotic Lesions who did not develop restenosis vs. who developed restenosis
$^\#$p = 0.002 Patients with Baseline Restenotic Lesions who did not develop restenosis vs. who developed restenosis
$^\delta$p = 0.01 Patients with Baseline Restenotic Lesions who did not develop restenosis vs. who developed restenosis

TABLE 4

Relative Risk of Restenosis by Quartiles

| | Quartiles | Relative Risk of Restenosis |
|---|---|---|
| Clot Strength (MA) | $1^{st}$ | 1 |
| | $2^{nd}$ | 2.5 |
| | $3^{rd}$ | 5 |
| | $4^{th}$ | 22.5 |
| Reaction Time (R) | $1^{st}$ | 1 |
| | $2^{nd}$ | 3 |
| | $3^{rd}$ | 4 |
| | $4^{th}$ | 2 |
| Coagulation Index (CI) | $1^{st}$ | 1 |
| | $2^{nd}$ | 3 |
| | $3^{rd}$ | 3 |
| | $4^{th}$ | 7 |

TABLE 5

Comparison of sensitivity and specificity of MA72 in predicting restenosis at 6 months post-PCI

| | Restenosis (n) | No Restenosis (n) | Total (n) | Odds Ratio |
|---|---|---|---|---|
| MA > 72 mm | 8 | 30 | 38 | 10.9 |
| MA ≤ 72 mm | 4 | 120 | 124 | — |
| Total | 12 | 150 | 162 | — |
| Sensitivity (%) | 67 | — | — | — |
| Specificity (%) | 80 | — | — | — |

TABLE 6

Stepwise multiple logistic regression analysis

| | Estimate | SE | p value | OR | 95% CI |
|---|---|---|---|---|---|
| Intercept | −2.25 | 1.87 | .2305 | — | — |
| Gender | 2.11 | 0.85 | .0129 | 8.26 | 1.57, 43.64 |
| Prior PTCA | −1.43 | 0.72 | .0478 | 0.24 | .06, .99 |
| Prior MI | −1.54 | 0.80 | .0542 | 0.21 | 0.05, 1.03 |
| MA72 | 2.39 | 0.79 | .0025 | 10.88 | 2.31, 51.19 |

No additional effects met the .05 significance level for inclusion in the model

The invention claimed is:

1. A method of selecting a stent for implantation in the circulatory system of a human being including the steps of:
    a) determining a threshold level of platelet coagulability of blood, above which a risk of restenosis is relatively high;
    b) obtaining a blood sample from a patient who requires implantation of a stent;
    c) testing said blood sample to determine platelet coagulability;
    d) comparing platelet coagulability of said blood sample with said threshold level;
    e) if said blood sample has a platelet coagulability level below said threshold level, selecting and implanting a bare metal stent, wherein antiproliferative therapy is not administered by means of the bare metal stent; and
    f) if said blood sample has a platelet coagulability level at or above said threshold level, selecting and implanting a drug-eluting stent.

2. The method of claim 1, wherein said determining step includes the step of obtaining blood samples from a multiplicity of people, testing each sample for platelet coagulability and correlating said samples with data regarding onset of restenosis among said people to determine said threshold level.

3. The method of claim 1, wherein a marker of platelet coagulability measured comprises platelet-fibrin mediated clot strength (MA).

4. The method of claim 3, wherein said threshold level is MA=72.

5. The method of claim 1, wherein said testing step comprises:
    obtaining a viscoelastic monitor and measuring clot strength of the blood sample, wherein the clot strength is a measure of platelet coagulability.

6. The method of claim 5, wherein said viscoelastic monitor includes automated analytical software.

7. The method of claim 6, wherein said software provides quantitative and qualitative measurements of initial fibrin formation, kinetics of clotting process, degree of platelet-fibrin mediated clot strength (MA), and dissolution.

8. The method of claim 5, wherein said blood sample is mixed with a clot-promoting substance.

9. The method of claim 8, wherein said substance comprises kaolin or thrombin.

10. The method of claim 3, wherein results from testing said sample samples are divided into quartiles sequentially numbered 1-4 from lowest to highest MA.

11. The method of claim 10, wherein patients having an MA in a $4^{th}$ said quartile are implanted with a drug-eluting stent.

12. The method of claim 10, wherein patients having an MA in a $1^{st}$ said quartile are implanted with a bare metal stent.

13. The method of claim 1, wherein a marker of platelet coagulability measured comprises speed of thrombin generation.

14. The method of claim 1, wherein a marker of platelet coagulability measured comprises platelet reactivity.

15. The method of claim 14, wherein said platelet reactivity is measured by an aggregometer.

16. The method of claim 14, wherein said platelet reactivity is measured by flow cytometry.

17. The method of claim 14, wherein platelet reactivity is measured by a device that quantitates viscoelastic properties.

18. The method of claim 1, wherein determining a threshold level of platelet coagulability comprises determining platelet-fibrin mediated clot strength (MA) or platelet hypercoaguability (PHC) of blood.

* * * * *